United States Patent [19]

Neufeld

[11] Patent Number: 5,073,755
[45] Date of Patent: Dec. 17, 1991

[54] METHOD AND APPARATUS FOR MEASURING THE ELECTRICAL PROPERTIES OF DIELECTRIC FILM IN THE GIGAHERTZ RANGE

[75] Inventor: Richard D. Neufeld, Vancouver, Canada

[73] Assignee: MPR Teltech Ltd., Burnaby, Canada

[21] Appl. No.: 495,043

[22] Filed: Mar. 19, 1990

[51] Int. Cl.$^5$ ............................................. G01N 22/00
[52] U.S. Cl. .................................... 324/632; 324/642; 333/161
[58] Field of Search ............... 324/629, 630, 632, 639, 324/641, 647, 642, 644; 333/161

[56] References Cited

U.S. PATENT DOCUMENTS

| | | | |
|---|---|---|---|
| 3,388,327 | 6/1968 | Sutton et al. | 324/647 |
| 3,796,976 | 3/1974 | Heng et al. | 333/161 |
| 4,123,703 | 10/1978 | Robinson | 324/632 |
| 4,520,308 | 5/1985 | Rohde et al. | 324/632 |
| 4,616,196 | 10/1986 | Sharma | 333/161 |
| 4,866,370 | 9/1989 | Flemming et al. | 324/639 |
| 4,942,373 | 7/1990 | Ozawa et al. | 333/161 |

OTHER PUBLICATIONS

Das et al., Two Methods for the Measurement of Substrate Dielectric Constant, 7-1987, IEEE Trans. on Micro. Theory and Tech., vol. MTT-35, No. 7, pp. 636–642.

*Primary Examiner*—Jack B. Harvey
*Attorney, Agent, or Firm*—Shlesinger Arkwright Garvey

[57] ABSTRACT

A dielectric test device formed on a substrate which includes a conductive ground plane layer formed over the substrate, a dielectric layer over the ground plane layer and a short and long conductive strip overlying the dielectric layer. Each of the long and short strips extends between common input and output conductive pads and are substantially identical in all respects except for length. Measurement of the interference pattern at the output node resulting from an input signal of a single frequency applied to the input node as frequency is varied over the gigahertz range allows the calculation of effective dielectric constant, propagation velocity as a function of frequency and attenuation.

11 Claims, 4 Drawing Sheets

METHOD AND APPARATUS FOR MEASURING THE ELECTRICAL PROPERTIES OF DIELECTRIC FILM IN THE GIGAHERTZ RANGE

BACKGROUND OF THE INVENTION

The present invention relates to a device and method for measuring the electrical properties of a dielectric film at frequencies in the Gigahertz range.

The progression towards VLSI chips with an increasing number of transistors of smaller and smaller dimensions has resulted in faster and faster signal transmission within such chips. This increased circuit speed has created a need for a method of interconnecting such chips without losing the benefit of this speed in the interconnecting lines. Thus, scientists have developed high density interconnects for use in interconnecting two or more product chips without suffering severe speed degradation. In the foregoing method an insulating substrate which is typically a silicon wafer is coated with a conducting material such as aluminum to form a ground plane over the wafer surface. A dielectric layer is deposited over the aluminum and then another aluminum layer deposited over the dielectric. The final aluminum layer is patterned to form bonding pads for the product chips and interconnecting lines. The electrical signal transmission properties depend critically on the performance of the dielectric. The relative dielectric constant and the radio frequency energy dissipation of the dielectric directly affect the speed and attenuation of a signal travelling along an interconnect line. The properties of the dielectric, in turn, depend on fabrication and environmental variables such as the cure profile and humidity. Consequently, a measurement circuit and procedure for monitoring the fabrication of high density interconnect circuits is needed.

At frequencies below 100 Megahertz there are many methods available to measure the electrical properties of a dielectric material. These methods are based on using the dielectric as the insulating layer in a capacitor structure. However, at Gigahertz (GHz) frequencies, a capacitor with a capacitance large enough to make measurement errors negligible is so reactive that it simply reflects all energy and yields no data on the value of the capacitance.

Other methods exist for measuring the properties of dielectrics in bulk form at GHz frequencies. These methods generally consist of inserting the bulk material into a wave guide structure and measuring the effect of the electrical behaviour of having the dielectric within the wave guide relative to having air in the wave guide. Two standard methods of measuring the dielectric properties are described in military specification MIL-P-13949F, Appendix I and Appendix II. The method of Appendix II is only applicable at frequencies below 100 Megahertz. The method of Appendix I uses a circuit fabricated using the dielectric material as the insulating layer, the critical part of the circuit being a half-wave resonator into which a small quantity of energy must be coupled in order to stimulate the resonance. A small portion of the energy stored in the resonating part of the circuit is tapped off and measured. For accurate measurements of the dielectric properties, the resonator should resonate with as little outside influence or loading as possible. The method of coupling energy into and out of the resonating part of the circuit is by means of a small non-conducting gap to the input and output connections. The difficulties arise if the dielectric film is so thin that the dimensions of the gap required for coupling are too small to reasonably fabricate. This is the case if the film thickness is on the order of 10 micrometers.

Another test is described by N.K. Das et al in a paper entitled "Two Methods for the Measurement of Substrate Dielectric Constant" which was published in the I.E.E.E. Transactions on Microwave Theory and Techniques, Volume MTT-35, No. 7, July, 1987, p. 636. In this article there is disclosed the characterization and comparison of two similar transmission lines. The two transmission lines are fabricated with the dielectric material as the insulating layer and with the transmission line dimensions except for length being as similar to each other as possible. Each of the transmission lines is mounted with separate input and output connections to the measurement equipment, and the electrical length and attenuation is then measured. The results are compared and the effects of the test jig should cancel, leaving only the electrical behaviour of the extra portion of the longer transmission line. The difficulty with this method is that errors are introduced by the inability to make the electrical connections to the transmission lines behave the same at GHz frequencies for both the short and the long line.

If the dielectric material to be characterized is in thin film form, with a thickness of less than 40 micrometers, and if the electrical properties of the material need to be determined at GHz frequencies, none of these measurement methods are suitable. Additionally, if the dielectric material and a production electrical circuit using the dielectric material are to be characterized, a test method which can be applied using the same substrate and structures similar to those of the production circuit is more useful than one that requires fabrication of a separate test sample.

Accordingly, it is an object of the present invention to produce an improved test device and method for measuring and determining the electrical properties of a thin film of dielectric material.

It is yet a further object of the present invention to produce a device of similar dimensions and on the same substrate as the high density interconnect structure in order to facilitate the estimation of the electrical properties of the product by testing only the test device.

SUMMARY OF THE INVENTION

According to the invention there is provided a dielectric test device formed on a substrate, which includes a conductive ground plane layer formed over the substrate, a dielectric layer over the ground plane layer and a short and a long conductive strip overlying the dielectric layer. Each of the short and long conductive strips extend between common input and output conductive pads with the strips being substantially identical in all respects which affect electrical properties except for length. The long strip is fabricated to be longer than the short strip.

Utilizing such a test device, particularly on a substrate in which other electrical circuits are formed, it is possible to excite the input pad or node with an electrical signal of a single frequency, have this signal propagate down each of the short and long conductive strips to the output pad or node, where the signals interfere to produce local maxima and minima as the frequency is varied from below one GHz up to a desired maximum frequency. The change in the signal amplitude at the output pad as a function of frequency allows the calculation of parameters such as effective dielectric constant and attenuation.

Preferably, the short and long strips have substantially identical bends and differ only in the length of corresponding straight sections. Such a device can be used as a process control monitor to check process variability. The "two-path circuit" allows propagation velocity and attenuation to be measured at suitably spaced frequency intervals. The frequencies of the peaks and valleys in the curve of response versus frequency gives the propagation velocity of the signal while the amplitude of the peaks and valleys gives the attenuation of those frequencies. The dielectric constant is calculated from the propagation velocity while the attenuation is calculated from the amplitude of the local maxima and minima.

The test device may be formed in a high density interconnect structure in which two or more standard product chips are mounted on a silicon substrate that has been coated with an electrically conductive ground plane overlaid by a dielectric such as polyamide and then a patterned aluminum interconnect network. Alternatively, the test device may be placed on a product chip to monitor the fabrication of dielectric layers on the latter.

BRIEF DESCRIPTION OF THE DRAWINGS

The novel features believed characteristic of the invention are set forth in the appended claims. The invention itself, however, as well as other features and advantages thereof, will be best understood by reference to the detailed description which follows, read in conjunction with the accompanying drawings, wherein:

DETAILED DESCRIPTION WITH REFERENCE TO THE DRAWINGS

Figure 1:
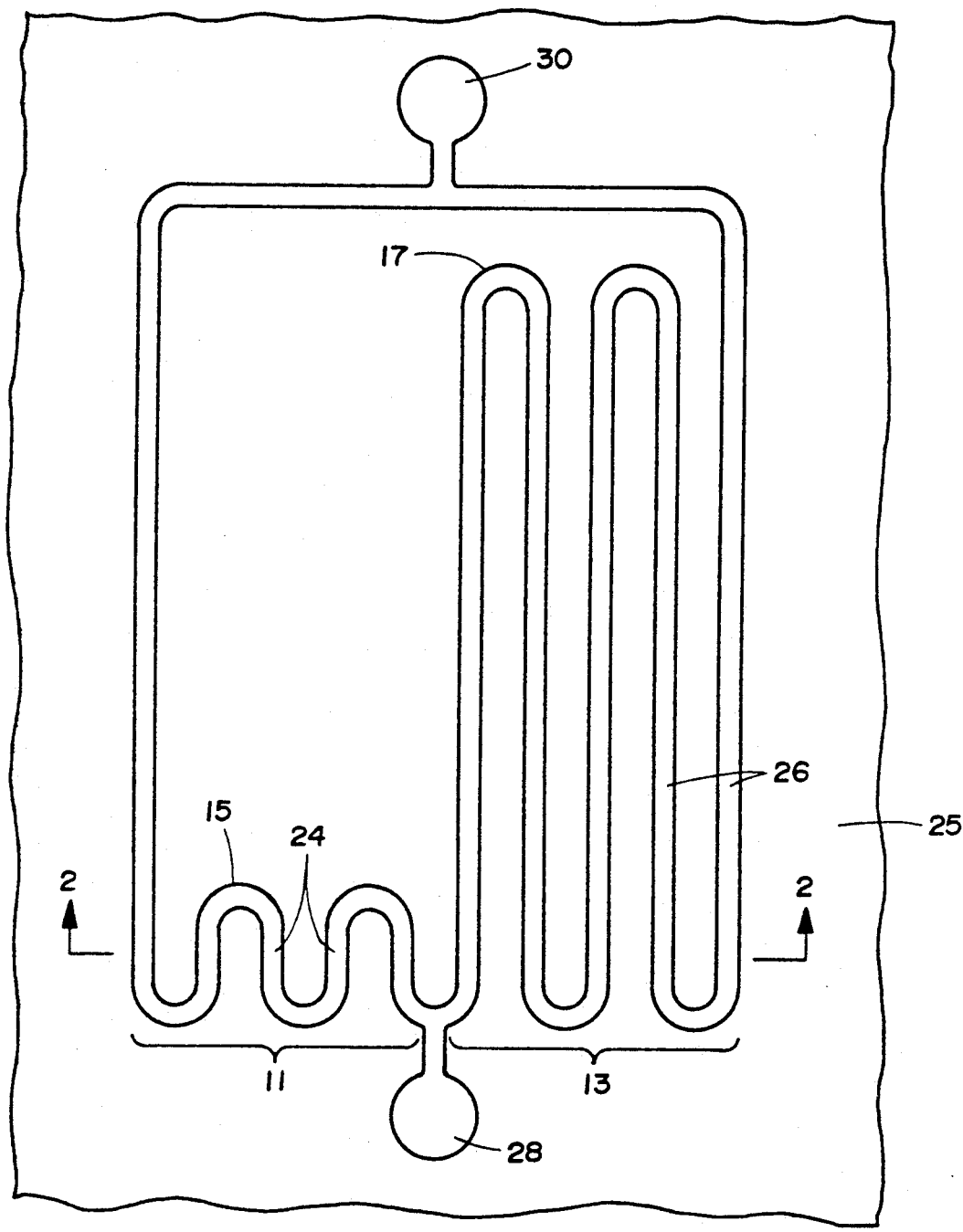
FIG. 1 is a plan view of the device showing a long and short transmission line coupled to common input and output nodes.

Referring to FIG. 1 there is shown a top view of a portion of a substrate having a short and a long transmission line or wave guide 11 and 13, respectively, formed thereon. The two transmission lines 11 and 13 are formed by a patterned conductor over a dielectric layer 25. The dielectric layer 25 is formed over an underlying layer of conductor 12 shown in FIGS. 2-4, which acts as an electrical ground plane. Transmission lines 11 and 13 join to a common input pad or node 28 and a common output pad or node 30. Short transmission line 11 consists of a plurality of straight, parallel sections or leads 24 joined in a serpentine arrangement by semi-circular end strips or bends 15. Similarly, long transmission line 13 consists of parallel straight sections or leads 26 joined by semi-circular end strips or bends 17. However, the straight sections 26 of long transmission line 13 are longer than the straight sections 24 of short transmission line 11.

Figure 6:
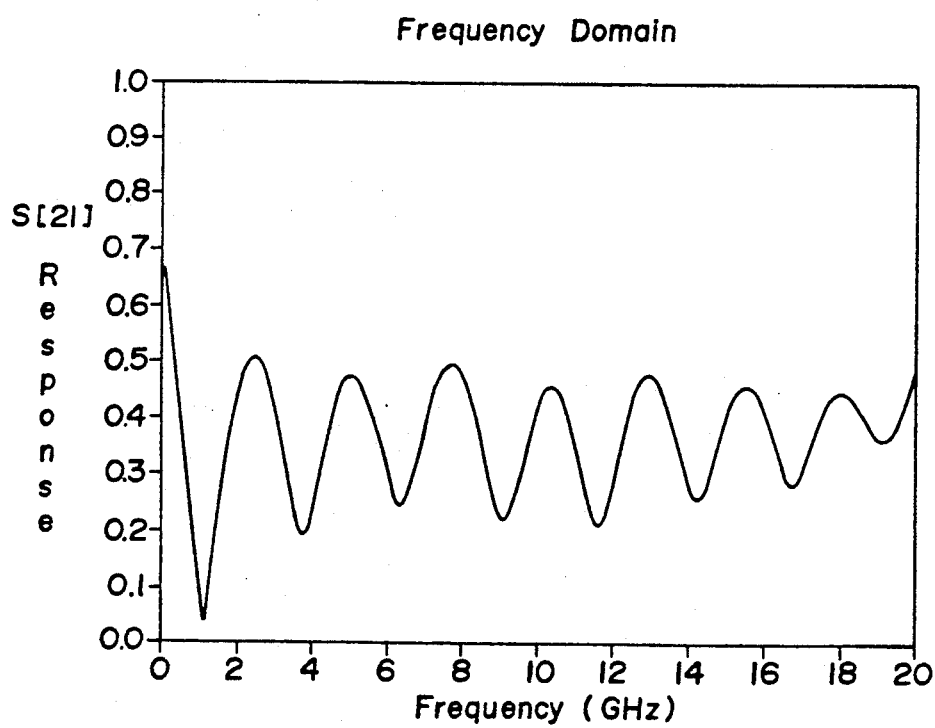
FIG. 6 is a frequency domain response at the output node arising from varying the frequency of a signal applied at the input node.

As pertaining to this invention, a short transmission lines is one long enough to accommodate bends identical to the bends in the long transmission line. A long transmission line should be long enough so as to produce a multiplicity of local minima and maxima in the frequency domain response (of which FIG. 6 is an example), yet not so long that the signal will be overly attenuated at the output, making measurement difficult.

Figure 2:
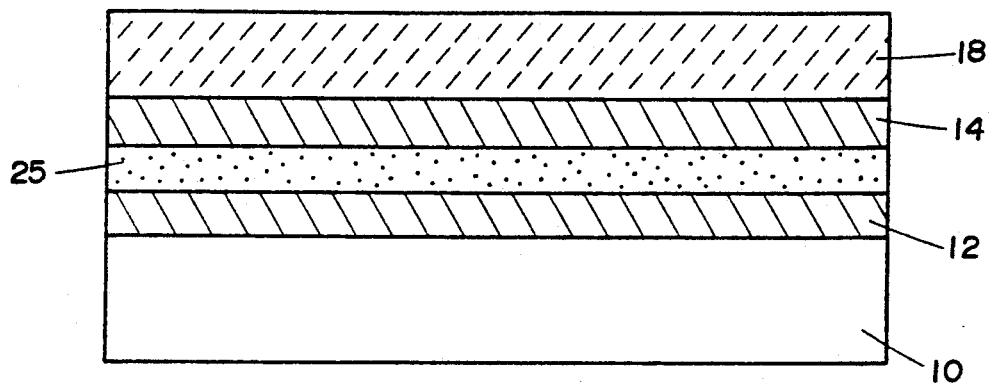
FIG. 2 is an elevation view in section taken along line 2—2 of FIG. 1 showing a portion of a substrate at an early stage in the fabrication of the transmission lines.
Figure 3:
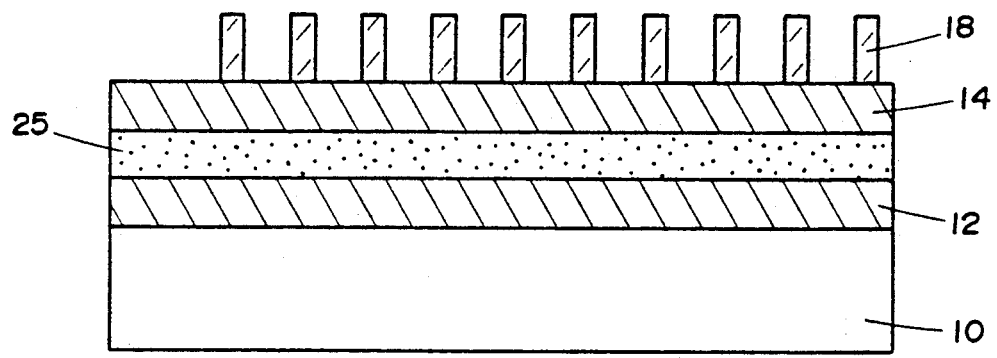
FIG. 3 shows the two transmission lines at an intermediate stage of development.
Figure 4:
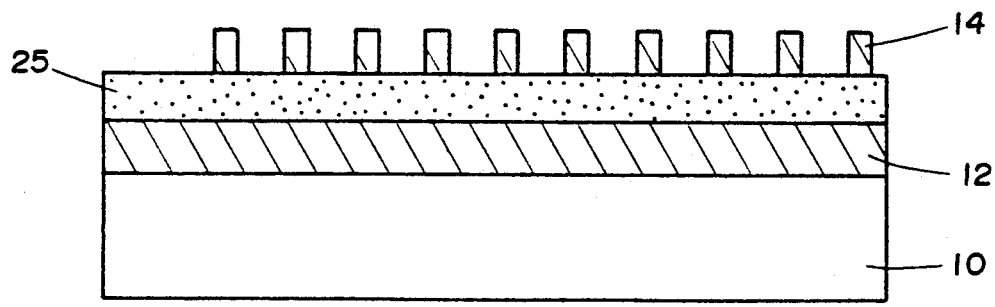
FIG. 4 shows the two transmission lines in section as a final step in the fabrication process.
Figure 5:
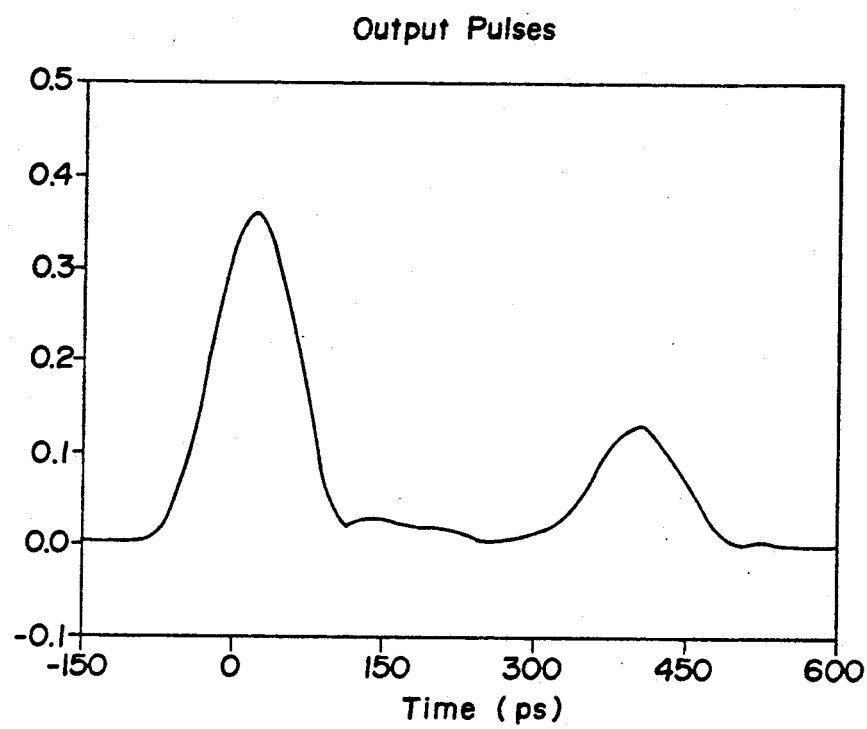
FIG. 5 is a time domain plot of pulses which are propagated down both the short and the long path.

Referring to FIGS. 2 to 4, there is shown a small portion of a substrate 10 used merely as a base for forming high density interconnects between standard chip products also mounted on the wafer but not shown. As seen in FIG. 2, a ground plane is formed by depositing a layer of conductor 12 over the surface of the entire wafer by known techniques. Next a layer of dielectric 25 is deposited over the conductor 12 and a second conductor layer 14 deposited over dielectric layer 25. A layer of photoresist 18 is applied over conductor layer 14 and patterned as shown in FIG. 3 with the pattern of the two transmission lines 11 and 13 and pads 28 and 30 shown in FIG. 1. Etching of the conductor layer 14 and removal of the photoresist yields the patterned leads shown in FIGS. 1 and 4.

The two transmission lines 11 and 13 are as identical as possible in the width of the upper conductor, which is made of conductor layer 14, in the thickness of the upper conductor, in the number of bends, the radius of the bends, surface roughness and all other features which affect wave guiding or transmission line properties except for that of length. Reactive ion etching of conductor layer 14 yields the most uniform lead properties of the upper conductor.

It is obvious that the usual environment for the foregoing transmission lines 11 and 13 is on a semi-conductor integrated circuit substrate. Such a circuit arrangement could be applied to a single semi-conductor product chip having thousands of other circuits.

Application to node 28 of an electrical signal of a single frequency, so as to generate a propagating signal in the two lines 11 and 13, results in the two divided signals being identical in amplitude, phase, propagation velocity and attenuation. However, because the signal on short line 11 travels a shorter distance than that on long line 13, on arrival at output node 30, the signal from long line 13 will be attenuated more than and retarded in phase relative to the signal from short line 11. The phase difference is given by the equation $$\Delta\phi = \beta L_L - \beta L_S = \beta \Delta L$$

where $L_L$ is the physical length of transmission line 13 and $L_S$ is the physical length of transmission line 11. The term $\beta$ is the phase-change coefficient, and is an important parameter in the analysis of the wave guiding behaviour of the transmission lines. As discussed in more detail by T.C. Edwards in "Foundations for Microstrip Circuit Design" (John Wylie & Sons Ltd., 1981), the phase-change coefficient $\beta$ is given according to the following:

$$\beta = \frac{2\pi}{\lambda g}$$

where λg is the length of the transmission line that the signal traverses to experience a phase shift of 2 π radians. Combining the equations and Δϕ and β, if the difference in physical lengths of the wave guides 11 and 13 is an integral multiple of the length λg, then the phase difference of the signals from the two transmission lines or wave guides at the output node 30 is a multiple of 2 π. In this case, the amplitude of the sensed signal will be locally maximized and will be equal to the scalar sum of the amplitudes of each of the signals on wave guides 11 and 13. If the difference in physical lengths of the wave guides is an odd integral multiple of half of the length λg, then the phase difference of the two signals is an odd integral multiple of π. In this case, the two signals will interfere destructively and the amplitude of the sensed signal will be locally minimized and will be equal to the scalar difference of the two signals. By sweeping the frequency of the signal stimulating the input node 28, the signal sensed at output node 30 will be alternately locally maximized and minimized. The frequencies of the local maxima and the local minima, and the signal amplitudes at these frequencies are recorded. Typically, a response as a function of frequency as shown in FIG. 6 is obtained. It will be observed that for the geometry corresponding to the example shown in FIG. 6, and where the difference in physical length of the short transmission line 24 and the long transmission line 26 is ΔL=71.1 mm, that as the frequency approaches approximately 1 GHz, a local minimum is first experienced in which the signals from the short and long transmission lines interfere destructively with a phase difference of π. As the frequency is increased to slightly more than 2 GHz constructive interference occurs as the phase difference become 2 π.

The velocity of propagation Vp may be calculated from the frequencies of the local extrema by either of the following two formulas:

$$\text{For local maxima: } Vp = \frac{f \Delta L}{m}$$

$$\text{For local minima: } Vp = \frac{f \Delta L}{m + \frac{1}{2}}$$

where f is the frequency of the signal stimulating the input node 28 and m is the number of minima below the frequency f at which the calculation of extremum velocity is being made.

The attenuation α of the signal in propagating a transmission line or wave guide of length L can be calculated by interpolating the amplitudes of the local maxima to generate the upper curve of the envelope and interpolating the amplitudes of the local minima to generate the lower curve of the envelope. The upper value of the envelope at a given frequency is $$e^{\alpha LS} + e^{\alpha LS} e^{\alpha \Delta L}$$

and the lower value of the envelope at a given frequency is $$e^{\alpha LS} - e^{\alpha LS} e^{\alpha \Delta L}$$

where e is the base of natural logarithms. The ratio of the lower value to the upper value is given as $$\frac{\text{lower value}}{\text{upper value}} = \frac{1 - e^{\alpha \Delta L}}{1 + e^{\alpha \Delta L}} = \tanh \frac{\alpha \Delta L}{2}$$

Inversion of the hyperbolic tangent term yields the attenuation of a waveguide of physical length ΔL.

Attenuation in Nepers per unit length is $$\alpha = \frac{2}{\Delta L} \tanh^{-1} \left( \frac{\text{lower value}}{\text{upper value}} \right)$$

A more commonly used unit of attenuation is dB, and since 1 Neper = 8.686 dB, the attentuation in dB per unit length is $$2 \frac{8.68}{\Delta L} \tanh^{-1} \left( \frac{\text{lower value}}{\text{upper value}} \right)$$

From the thus determined values of the propagation velocity and the attenuation, the electrical properties can be calculated. For example, for a ΔL value of 71.1 mm at the frequency of 2.43 GHz, the propagation velocity Vp is given by the following:

$$Vp = f \Delta L = 2.465 \times 71.1 = 0.175 \text{ mm/ps}$$

The effective dielectric constant at that frequency is given by the following:

$$\epsilon_{\text{effective}} = (CVp^{-1.2}$$

where C is the velocity of light. The dielectric constant in the above equation is the effective dielectric constant and is a function of the bulk dielectric constant ε which can be obtained in a capacitance measurement with a capacitor of known dimensions formed by upper and lower conductive plates separated by the dielectric. The two constants are related by a shape factor which can be calculated using the geometry of the lead lines 24 and 26 through a complicated formula.

Figure 7:
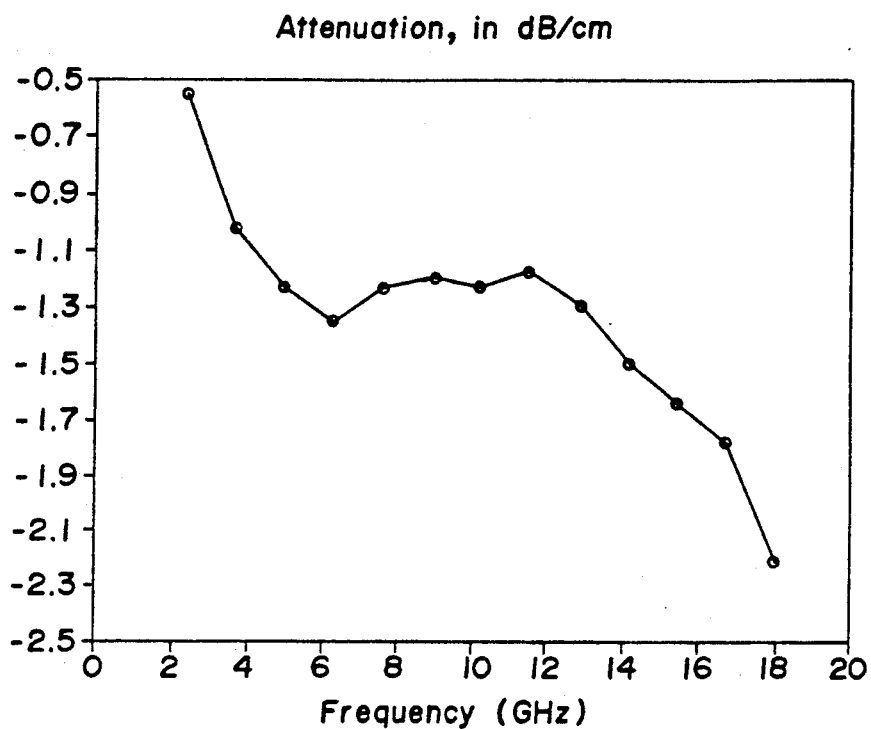
FIG. 7 is a graph of attenuation extracted from the results of FIG. 6.
Figure 8:
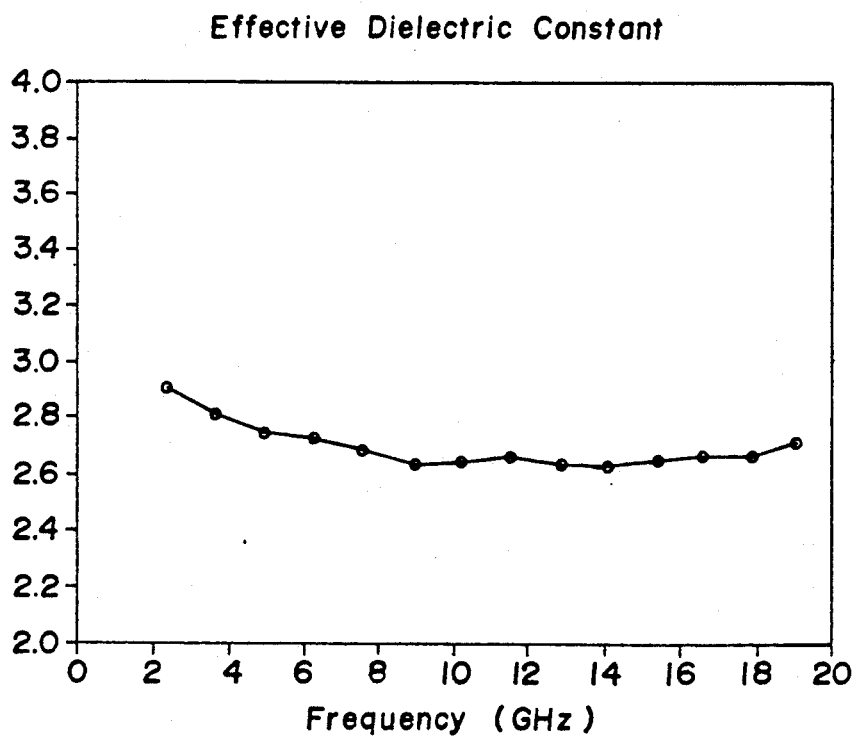
FIG. 8 is a graph of effective dielectric constant extracted from the results in FIG. 6.

For the specific examples used in the preceding calculations of attenuation and effective dielectric constant, further measurements and calculations yield the graphs of attenuation varying with frequency in FIG. 7 and effective dielectric constant variation with frequency in FIG. 8.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

I claim:

1. A dielectric test device formed on a substrate, comprising:
   (a) a conductive ground plane layer formed over said substrate;
   (b) a dielectric layer over said ground plane layer;
   (c) a short and a long conductive strip overlying said dielectric layer, each of said strips being substantially identical in all respects which affect wave guide properties except for length with said long strip being longer than said short strip;

(d) means for coupling identical input signals of a single frequency and the same amplitude and phase to an input end of each of said short and long conductive strips; and (e) a common output pad at an output end of each of said short and long strips for adding together said signals after propagation down said short and long conductive strips.

2. A dielectric test device according to claim 1, wherein said input coupling means is an input conductive pad connected to input ends of said long and short conductive strips.

3. A dielectric test device formed on a substrate, comprising:

(a) a conductive ground plane layer formed over said substrate;

(b) a dielectric layer over said ground plane layer; and (c) a short and a long conductive strip overlying said dielectric layer, each of said strips extending between common input and output conductive pads, said strips being substantially identical in all respects which affect wave guide properties except for length and said long strip being longer than said short strip.

4. A dielectric test device according to claim 3, wherein said short and long strips have substantially identical bends and differ only in the length of corresponding straight sections.

5. A dielectric test device according to claim 3, wherein each of said short and long conductive strips is formed into a serpentine pattern with parallel straight sections and semi-circular end connections to adjacent sections.

6. A dielectric test device according to claim 3, wherein the dielectric material is an organic resin.

7. A dielectric test device according to claim 3, wherein the dielectric material is polyamide.

8. A dielectric test device according to claim 3, wherein said substrate is a silicon wafer.

9. A dielectric test device according to claim 3, wherein said conductive ground plane and strips are aluminum.

10. A method of measuring the electrical properties of a dielectric film at frequencies in the Gigahertz range utilizing two transmission lines formed using the dielectric, the lines having substantially identical physical and electrical properties except for length, comprising:

(a) electrically stimulating the input ends of said transmission lines with a signal of a single frequency so as to generate a propagating signal along each of the two transmission lines;

(b) varying the frequency from near zero up to a maximum frequency at which measurements are to be made; and (c) adding together the signals after propagation along said long and short transmission by directing them to a common output pad; and (d) detecting and measuring the added signals.

11. A method of measuring the electrical properties of a dielectric film at frequencies in the Gigahertz range utilizing two transmission lines of different length formed by a conductive layer, a ground plane and a dielectric film between the ground plane and the transmission lines with the two transmission lines except for length having substantially identical physical properties and common input and output pads, comprising:

(a) electrically stimulating the input pad with a microwave input, signal of a single frequency so as to generate a propagating signal along each of the two transmission lines;

(b) detecting the resultant signal at the output pad; and (c) varying the frequency of said input signal from below a first frequency producing at the output pad minimum and maximum output signals for recordation.

* * * * *